United States Patent
Ziegler et al.

(10) Patent No.: US 8,293,712 B2
(45) Date of Patent: Oct. 23, 2012

(54) COSMETIC COMPOSITION FOR STIMULATING THE SYNTHESIS OF PROTEINS OF THE BASEMENT MEMBRANE

(75) Inventors: Hugo Ziegler, Witterswil (CH); Dominik Imfeld, Münchenstein (CH); Martin Stöckli, Burg Im Leimental (CH); Marc Heidl, Grenzach-Whylen (DE)

(73) Assignee: DSM IP Assets B.V., Heerlen (NL)

( * ) Notice: Subject to any disclaimer, the term of this patent is extended or adjusted under 35 U.S.C. 154(b) by 219 days.

(21) Appl. No.: 12/226,191

(22) PCT Filed: Apr. 28, 2006

(86) PCT No.: PCT/EP2006/003998
§ 371 (c)(1),
(2), (4) Date: Dec. 10, 2008

(87) PCT Pub. No.: WO2007/124770
PCT Pub. Date: Nov. 8, 2007

(65) Prior Publication Data
US 2009/0155347 A1    Jun. 18, 2009

(51) Int. Cl.
*A61K 38/39* (2006.01)
*A61K 38/00* (2006.01)
*A61K 31/74* (2006.01)

(52) U.S. Cl. ............ 514/17.2; 514/18.8; 424/78.08

(58) Field of Classification Search ......... 514/17.2, 514/18.8; 424/78.08
See application file for complete search history.

(56) References Cited

U.S. PATENT DOCUMENTS

| 5,939,082 | A | 8/1999 | Oblong et al. |
| 2005/0065090 | A1 | 3/2005 | Ludin et al. |
| 2007/0099842 | A1 | 5/2007 | Ziegler et al. |
| 2007/0248587 | A1 * | 10/2007 | Cruse ............ 424/94.65 |

FOREIGN PATENT DOCUMENTS

| EP | 1 640 041 A2 | 3/2006 |
| WO | WO-97/39733 A1 | 10/1997 |
| WO | WO-03/037933 A2 | 5/2003 |
| WO | WO-2004/099237 A1 | 11/2004 |

* cited by examiner

*Primary Examiner* — Benjamin Packard
*Assistant Examiner* — Adam C Milligan
(74) *Attorney, Agent, or Firm* — Nixon & Vanderhye P.C.

(57) ABSTRACT

Cosmetic composition which can be applied topically, comprising at least one compound of the general formula (I) in which $R^1$ is H, $C_1$-$C_{20}$-alkyl, cycloalkyl or aryl-$C_1$-$C_4$-alkyl, n is 1-4, X is —O—, —NH— or —$NR^2$— and $R^2$H or $C_1$-$C_{20}$-alkyl; and at least one compound corresponding to the above formula (I) but in which $XR^1$ with X having the possible meaning of —NH— is the residue of an alpha-amino acid; use of these compounds and of the composition for stimulating the synthesis of the proteins of the basement membrane; and also both those compounds of the formula (I) in which X is —$NR^2$— and both $R^1$ and $R^2$ are different from H, and the compounds corresponding to formula (I) but in which $XR^1$ with X having the possible meaning of —NH— is the residue of an alpha-amino acid, as such.

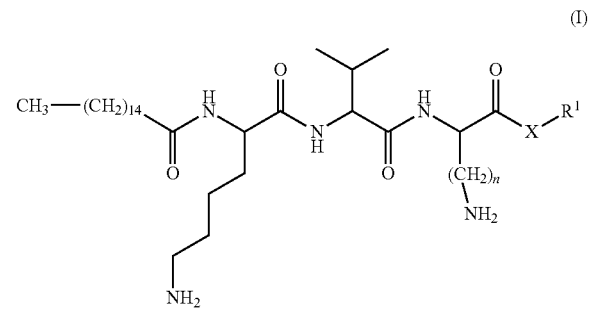

(I)

12 Claims, No Drawings

COSMETIC COMPOSITION FOR STIMULATING THE SYNTHESIS OF PROTEINS OF THE BASEMENT MEMBRANE

The present invention relates to a cosmetic composition, in particular a cosmetic composition which can be applied topically, comprising at least two particular peptide derivatives, for stimulating the synthesis of molecules of the basement membrane, in particular proteins thereof, and the use of these particular peptide derivatives for stimulating the synthesis of molecules of the basement membrane, in particular proteins thereof.

The basement membrane (BM) on the dermal-epidermal join has several functions, of which the most obvious function is close joining of the epidermis to the dermis, and in this way ensures mechanically stable cohesion of the two layers of tissue. The "polarity" and the construction of the epidermis are also influenced by the basement membrane, and at the same time the BM is a clear demarcation between the epidermis and dermis. It is assumed that the BM initiates epidermal differentiation of keratinocytes and maintains the proliferative state of the basal cell layer. Under normal conditions the BM also prevents direct contact of epidermal cells with the dermis. After an injury with damage to the BM, however, direct contact with the dermis arises, after which the cells change their behaviour and initiate the wound healing process.

A further important function of the BM is correct communication between the epidermal and dermal cells. Since the epidermis and the dermis do not function independently of one another, normal skin homeostasis requires regular passage of biochemical signals in both directions between the two cell types. In general, this is small molecules which are produced in one compartment and must be transported selectively via the BM in order to pass their "message" to the other side. In this context, the BM has the important function of acting as an active filter and of passing on the signal molecules or just blocking them as required. Correctly functioning epidermal-dermal communication via the BM is essential for the skin.

The BM itself can in turn be divided morphologically into three layers, the lamina lucida, the lamina densa and the lamina fibroreticularis. The lamina lucida is the region between the epidermal cells and the lamina densa and contains the hemidesmosomes, which are visible in the BM as electron-dense plaques. The hemidesmosomes join the basal keratinocytes, which are capable of proliferation, to the BM and are built up, inter alia, from collagen XVII (or bp180) and the integrins alpha6/beta4. Deletions in collagen XVII can lead to fragile skin with frequent blistering (epidermolysis bullosa simplex). The lamina densa is a flat structure (sheet) consisting chiefly of collagen IV.

Constituents of the BM are essentially proteins, proteoglycans and glycosaminoglycans. One of the important components of the anchoring complex is laminin V. Laminin V is, inter alia, essential for epidermal adhesion to the dermal tissue, since mutations in laminin V likewise lead to severe forms of blistering of the skin (Herlitz's junctional epidermolysis bullosa). Laminin V binds the transmembrane integrins alpha6/beta4 of the hemidesmosomes on the one hand, and on the other hand laminin V is joined to collagen VII, which in turn forms anchoring fibrils into the dermis. Collagen VII is the main component of the lamina fibroreticularis. The structural proteins collagen IV, VII, XVII and laminin V and the integrins alpha6, beta4 are accordingly, alongside further proteins, essential main components for construction of the BM and the hemidesmosomes and are therefore important for the correct and diverse functions of the BM in the skin.

It is known that endogenous (age-related) or exogenous (light-related) ageing manifests itself in an irreversible degeneration of the tissue, in particular the skin, and becomes increasingly visible macroscopically in the form of wrinkles, flabbiness, rough surface, irregular pigmentation etc. These changes arise due to a reduction in the anabolic reactions (syntheses) and an increase in the catabolic reactions (breakdown) of collagens and inter alia also the protein components of the BM. Histologically visible changes are concentration of shortened unstructured elastin fibres (elastosis), a reduction in collagen fibres, infiltration of inflammation mediators and atrophy of the epidermis with atypical nonpolar keratinocytes. For example, the number of anchoring fibrils from the BM into the dermis and the amount of collagen VII, which the fibrils are made of, decrease rapidly in skin aged by light, and the stability of the binding of the BM to the dermis is therefore impaired. The other proteins of the BM also partly go into remission in ageing skin and the structural organization of the BM degenerates with increasing age.

The structural proteins of the BM mentioned are predominantly expressed by keratinocytes and partly also by fibroblasts. The synthesis reactions in the skin matrix are chiefly regulated by polypeptides, the so-called growth factors and cytokines. Among these peptides, TGF-β1 is one of the most important regulators involved in the synthesis reactions of this skin matrix. It is also secreted in the matrix by keratinocytes and fibroblasts. Externally supplied active compounds which stimulate synthesis of the BM proteins could on the one hand compensate age-related degenerations of the BM and also already have a preventive character by slowing down the decrease in the BM protein content associated with ageing.

It has now been found that, surprisingly, a clear improvement in the appearance of the skin and a slowing down of age-related breakdown of the basement membrane proteins are successfully achieved with a combination of at least one particular cosmetically active tri- and at least one particular cosmetically active tetrapeptide derivative (called "compounds according to the invention" in the following) which are present in cosmetic compositions which can be applied topically. This is effected since the compounds according to the invention can be diffused rapidly and in a sufficient concentration through the stratum corneum and the epidermis to the site of action in the boundary region between the epidermis and dermis and bring about there a rapid and powerful stimulation of the synthesis of the proteins of the basement membrane there. It can thus be demonstrated that the concentration of collagen IV, VII, XVII, laminin V and that of integrin beta4 is increased significantly with a combination of at least one particular tripeptide derivative and at least one particular tetrapeptide derivative.

The present invention is defined in the claims. In particular, the present invention relates to a cosmetic composition, in particular a cosmetic composition which can be applied topically, comprising at least one compound of the general formula (I)

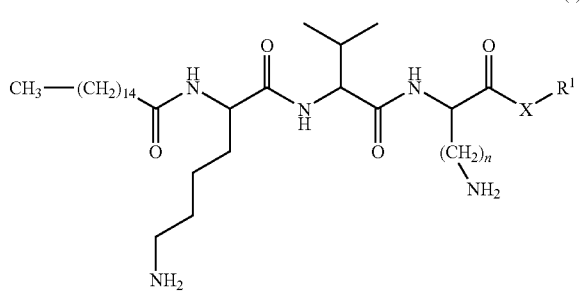

wherein
R¹ denotes H, $C_1$-$C_{20}$-alkyl, cycloalkyl or aryl-$C_1$-$C_4$-alkyl,
n denotes 1-4,
X denotes —O—, —NH— or —NR²— and
R² denotes H or $C_1$-$C_{20}$-alkyl;
and at least one compound corresponding to the above formula (I), but wherein
XR¹ with X in the possible meaning —NH— denotes the radical of an alpha-amino acid.

The present invention also relates to the use of the compounds of the above formula (I) together with compounds corresponding to the above formula (I), but wherein XR¹ with X in the possible meaning —NH— denotes the radical of an alpha-amino acid, for the preparation of the composition defined above and the use thereof for stimulating the synthesis of molecules of the basement membrane, in particular proteins thereof.

The present invention also relates to the use of the compounds of the above formula (I) together with compounds corresponding to the above formula (I), but wherein XR¹ with X in the possible meaning —NH— denotes the radical of an alpha-amino acid, for stimulating the synthesis of molecules of the basement membrane, in particular proteins thereof.

The present invention also relates to those compounds of the above general formula (I) wherein X denotes —NR²— and both R¹ and R² are other than H, and also the compounds corresponding to the above general formula (I), but wherein XR¹ with X in the possible meaning —NH— denotes the radical of an alpha-amino acid, as such.

In the compounds of the formula (I) and in the compounds corresponding to the above general formula (I), but wherein XR¹ with X in the possible meaning —NH— denotes the radical of an alpha-amino acid, the amino acids can be present as racemates or in their enantiomerically pure L and D form.

The general expressions used above are defined as follows:
"Alkyl" is to be understood as meaning both linear and branched saturated hydrocarbon radicals. Examples are methyl, ethyl, propyl, n-butyl, n-pentyl, n-hexyl, n-heptyl, n-octyl, n-nonyl, n-undecanyl, n-dodecanyl, n-tridecanyl, n-hexadecanyl, n-heptadecanyl, n-octadecanyl or n-nonadecanyl as unbranched and isopropyl, tert-butyl, isobutyl, sec-butyl or isoamyl as branched radicals.

"Cycloalkyl" is to be understood as meaning cyclic saturated hydrocarbon radicals having up to 8 carbon atoms, such as, for example, cyclopropyl, cyclobutyl, cyclopentyl, cyclohexyl or cycloheptyl.

"Aryl" is to be understood as meaning aromatic, mono- or polynuclear hydrocarbon radicals having up to 10 carbon atoms, which can be mono- or polysubstituted by, for example, alkyl, alkoxy, halogen and/or trifluoromethyl, such as, for example, phenyl, p-tolyl, o-tolyl, m-tolyl, 3,4-dimethoxyphenyl, 2-naphthyl or 3-naphthyl. "Aryl" furthermore also includes radicals of heteroaryl groups, i.e. of optionally correspondingly substituted mono- or polynuclear aromatic heterocyclic radicals, such as, for example, 2-pyridyl, 3-pyridyl, 4-pyridyl, 2-quinolinyl or 3-isoquinolinyl.

The compounds according to the invention can form mono- or polyvalent, uniform or mixed salts with acids, e.g. with inorganic acids, such as hydrogen chloride, hydrogen bromide, sulfuric acid or phosphoric acid; or with suitable carboxylic acids, e.g. aliphatic mono- or dicarboxylic acids, such as formic acid, acetic acid, trifluoroacetic acid, trichloroacetic acid, propionic acid, glycollic acid, succinic acid, fumaric acid, malonic acid, maleic acid, oxalic acid, phthalic acid, citric acid, lactic acid or tartaric acid; or with aromatic carboxylic acids, such as benzoic acid or salicylic acid; or with aromatic-aliphatic carboxylic acids, such as mandelic acid or cinnamic acid; or with heteroaromatic carboxylic acids, such as nicotinic acid; or with aliphatic or aromatic sulfonic acids, such as methanesulfonic acid or toluene sulfonic acid. Dermatologically acceptable salts are preferred.

The general formula (I) includes all the isomeric forms and mixtures thereof, e.g. racemic mixtures and mixtures of rotamers.

Combinations of compounds of the general formula (I) wherein R¹ denotes H or $C_1$-$C_{20}$-alkyl, n denotes 2 or 4 and X denotes oxygen with compounds corresponding to the general formula (I), but wherein XR¹ with X in the possible meaning —NH—denotes the radical of a natural alpha-amino acid and n denotes 2 are preferred.

The combinations of compounds of the following Table 1 are particularly preferred:

| | |
|---|---|
| 1.1 | Palm-Lys-Val-Lys-OH |
| 1.2 | Palm-Lys-Val-Orn-OH |
| 1.3 | Palm-Lys-Val-Dab-OH |
| 1.4 | Palm-Lys-Val-Dab-OMe |
| 1.5 | Palm-Lys-Val-Dab-Ooctyl |
| 1.6 | Palm-Lys-Val-Dab-Ocetyl |
| 1.7 | Palm-Lys-Val-Dab-$NH_2$ |
| 1.8 | Palm-Lys-Val-Dab-NHbutyl |
| 1.9 | Palm-Lys-Val-Dab-N(butyl)$_2$ |
| 1.10 | Palm-Lys-Val-Dab-NHoctyl |
| 1.11 | Palm-Lys-Val-Dab-N(octyl)$_2$ |
| 1.12 | Palm-Lys-Val-Dab-NHcetyl |
| 1.13 or | Palm-Lys-Val-Dab-N(cetyl)$_2$ |
| 1.14 with | Palm-Lys-Val-Dap-OH |
| 2.1 | Palm-Lys-Val-Lys-Ala-OH |
| 2.2 | Palm-Lys-Val-Lys-Arg-OH |
| 2.3 | Palm-Lys-Val-Lys-Gln-OH |
| 2.4 | Palm-Lys-Val-Lys-Ser-OH |
| 2.5 | Palm-Lys-Val-Dab-Glu-OH |
| 2.6 | Palm-Lys-Val-Dab-Asp-OH |

| 2.7 | Palm-Lys-Val-Dab-Thr-OH |
| --- | --- |
| 2.8 | Palm-Lys-Val-Dab-Lys-OH |
| 2.9 | Palm-Lys-Val-Dab-Met-OH |
| 2.10 | Palm-Lys-Val-Dab-Asn-OH |
| 2.11 | Palm-Lys-Val-Dab-His-OH |
| 2.12 or | Palm-Lys-Val-Dab-Nle-OH |
| 2.13 | Palm-Lys-Val-Dab-Phe-OH |

Very particularly preferred combination partners are Palm-Lys-Val-Dab-OH (1.3) and Palm-Lys-Val-Dab-Thr-OH (2.7).

The compounds according to the invention can be used in concentrations which vary between 0.5 and 5,000 ppm (w/w), preferably between 1 and 1,000 ppm (w/w) in the cosmetic end product.

The compounds according to the invention can be used in the form of a solution, a dispersion or an emulsion or encapsulated in carriers, such as macro-, micro- or nanocapsules, in liposomes or chylomicrons, or enclosed in macro-, micro- or nanoparticles or in microsponges or absorbed on pulverulent organic polymers, talc, bentonite and other mineral carriers.

The compounds according to the invention can be used in any galenical form: oil/water and water/oil emulsions, milk, lotions, ointments, gelling and viscous, surface-active and emulsifying polymers, pomades, shampoos, soaps, gels, powders, sticks and pencils, sprays, body oils, face masks, patches.

The compounds according to the invention can be used with any other constituent conventionally used. Such compositions can comprise extracted lipids and/or synthetic lipids, gelling and viscous, surface-active and emulsifying polymers, water- or fat-soluble active principles, plant extracts, tissue extracts, marine extracts, sunscreen agents, antioxidants, moisture-retaining and barrier agents, skin revitalizing active compounds, additional skin care active compounds or skin protection agents.

The compounds according to the invention can be used in combination with any other cosmetic skin care active compound conventionally used. There may be mentioned by way of example of an additional skin care active compound antiwrinkle active compounds/anti-atrophy active compounds: The composition according to the invention can comprise a safe and active amount of one or more antiwrinkle active compounds or anti-atrophy active compounds. Examples of antiwrinkle/anti-atrophy active compounds which are suitable for use in the compositions according to the invention include sulfur-containing D- and L-amino acids and their derivatives and salts, in particular the N-acetyl derivatives, a preferred examples of these being N-acetyl-L-cysteine; thiols; hydroxy acids (e.g. α-hydroxy acids, such as lactic acid and glycollic acid, or β-hydroxy acids, such as salicylic acid and salicylic acid derivatives, such as octanoyl derivatives), phytic acid, liponic acid; lysophosphatidic acid, skin peeling agents (e.g. phenol and the like), vitamin $B_3$ compounds and retinoids, which improve the advantages of the present invention for smoothing of the skin.

a) Vitamin B3 Compounds

The compositions according to the invention can comprise a safe and active amount of a vitamin B3 compound. Vitamin B3 compounds are particularly useful for regulating the state of the skin, as is described in the US patent application pending at the same time with application Ser. No. 08/834,010, filed on 11 Apr. 1997 (corresponding to international publication WO 97/39733 A1, published on 30 Oct. 1997). Examples of derivatives of the vitamin B3 compounds mentioned include nicotinic acid esters, including non-vasodilating esters of nicotinic acid (e.g. tocopheryl nicotinate), nicotinylamino acids, nicotinyl alcohol esters of carboxylic acids, nicotinic acid N-oxide and niacinamide N-oxide.

b) Retinoids

The compositions according to the invention can also comprise a retinoid. "Retinoid", as used here, includes all natural and/or synthetic analogues of vitamin A or retinol-like compounds which have the biological activity of vitamin A in the skin, and the geometric isomers and stereoisomers of these compounds. The retinoid is preferably retinol, retinol esters (e.g. $C_2$- to $C_{22}$-alkyl esters of retinol, including retinyl palmitate, retinyl acetate, retinyl propionate), retinal and/or retic acid (including all-trans retic acid and/or 13-cis retic acid), in particular retinoids other than retic acid. Other suitable retinoids are tocopheryl retinoate [tocopherol ester of retic acid (trans or cis)], adaptalene {6-[3-(1-adamantyl)-4-methoxyphenyl]-2-naphthoic acid} and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The compositions according to the invention can comprise a safe and active amount of the retinoid, so that the resulting composition is safe and active for regulating the state of horny tissue, preferably for regulating visible and/or palpable discontinuities of the skin, in particular for regulating signs of ageing of the skin, more preferably for regulating visible and/or palpable discontinuities of the nature of the skin surface related to ageing of the skin.

c) Hydroxy Acids

The compositions according to the invention can comprise a safe and active amount of a hydroxy acid. Preferred hydroxy acids for use in the compositions according to the invention include salicylic-acid and salicylic acid derivatives.

d) Peptides

The compositions according to the invention can comprise at least one additional peptide, including, but not limited to, di-, tri-, tetra-, penta- and hexapeptides. Such peptides and/or derivatives thereof can be added to the compositions according to the invention in safe and active amounts. "Peptides" here refers to both the naturally occurring peptides and the synthetic peptides and also includes peptidomimetics and metal complexes of "peptides". The naturally occurring and commercially obtainable compositions which comprise peptides can also be used here.

Dipeptides which are suitable for use in the compositions according to the invention include carnosine (β-Ala-His). Tripeptides which are suitable for this include Gly-His-Lys, Arg-Lys-Arg and His-Gly-Gly. Preferred tripeptides and derivatives thereof include palmitoyl-Gly-His-Lys, which can be acquired as Biopeptide CL™ (100 ppm palmitoyl-Gly-His-Lys, commercially obtainable from Sederma, France), peptide CK (Arg-Lys-Arg), peptide CK+ (ac-Arg-Lys-Arg-NH2) and β-Ala-Pro-Dab-NH-benzyl, which is marketed under the name SYN®-AKE by Pentapharm, Switzerland. Tetrapeptides which are suitable for use in the compositions according to the invention include peptide E. Examples of suitable pentapeptides are Matrixyl (palmitoyl-Lys-Thr-Thr-Lys-Ser), obtainable from Sederma, France, and those described in WO 03/037933 (Pentapharm, Switzerland). A hexapeptide which is suitable for use is Argireline (Ac-Glu-Glu-Met-Gln-Arg-Arg-NH2), manufactured by Lipotec, Spain.

The compounds according to the invention and the cosmetic compositions comprising them are employed for skin care products, in particular for improving the appearance of the skin and against adverse effects of ageing of the skin caused by breakdown of the proteins of the basement membrane.

The following examples are intended to explain the invention without limiting it. Abbreviations used in the text and in Examples 1-9 mean AcOH: Acetic acid
ACN: Acetonitrile
AB: Antibody
Ala: Alanine
Arg: Arginine
Asn: Asparagine
Asp: Aspartic acid
Boc: tert-Butoxycarbonyl
BSA: Bovine serum albumin
CTR: Chlorotrityl resin
Dab: 2,4-Diaminobutyric acid
Dap: 2,3-Diaminopropionic acid
DBU: 1,8-Diazabicyclo[5,4,0]undec-7-ene (1, 5-5)
DCC: N,N'-Dicyclohexylcarbodiimide
MC: methylene chloride
DIC: N,N'-Diisopropylcarbodiimide
DIPEA: Diisopropylethylamine
DMEM: Dulbecco's Modified Eagle Medium
DMF: Dimethylformamide
EM: Electron microscope
EtOAc: Ethyl acetate
FCS: Foetal calf serum
Fmoc: 9-Fluorenylmethoxycarbonyl
GF/A: Glass fibre microfilter
Gln: Glutamine
Glu: Glutamic acid
HaCaT: Human immortalized keratinocytes
HOBt: 1-Hydroxybenzotriazole
ILe: Isoleucine
LH20: Amersham size exclusion resin
Lys: Lysine
Met: Methionine
MS: Mass spectrometry
NMM: N-Methylmorpholine
NMR: Nuclear magnetic resonance
Nle: Norleucine
Orn: Ornithine
Palm: Palmitoyl
PBS: Phosphate buffered saline
PE: Petroleum ether
Phe: Phenylalanine
RT: room temperature.
Ser: Serine
tBu: tert-butyl
TBTU: O-(Benzotriazol-1-yl)-N,N,N',N'-tetramethyluronium tetrafluoroborate
TCTU: O-(1H-6-Chlorobenzotriazol-1-yl)-1,1,3,3-tetramethyluronium hexafluorophosphate
TGF-$\beta$1/2: Transforming growth factor $\beta$1 or $\beta$2
TFA: Trifluoroacetic acid
THF: Tetrahydrofuran
Thr: Threonine
Tris: Tris-(hydroxymethyl)-aminomethane
Tween 20: Polyethylene glycol sorbitan monolaurate solution
Val: Valine
Z: Benzyloxycarbonyl

EXAMPLE 1

Determination of the Stimulation of Laminin V Synthesis in Keratinocyte Cell Cultures of the Cell Line HaCaT by Treatment with the Peptide Derivatives According to the Invention The laminin V production per cell of HaCaT keratinocytes cultured in vitro was detected by means of an ELISA (enzyme-linked immunosorbent assay). The increase in laminin V production by the cells in the presence of the peptidic active compounds was quantified by this method.

The human HaCaT keratinocytes were donated by Prof. Fusenig of the Deutsche Krebsforschungszentrum in Heidelberg and were cultured in culture medium by standard cell culture methods. After an incubation time of 72 hours with the corresponding peptides (active compound), the quantitative determination is carried out with an antibody specific for laminin V. After determination of the laminin V content, the cell count is determined by means of the CyQUANT® from Molecular Probes. The laminin V content per cell is calculated as units from the individual values.

Material:

| Culture medium: |
| --- |
| DMEM |
| 10% FCS |
| 100 IU/ml penicillin |
| 0.1 mg/ml streptomycin |
| Wash buffer: |
| 0.05 M Tris, pH 8.5 |
| 0.15 M NaCl |
| 0.1% BSA |
| 0.1% Tween 20 |
| AB dilution solution: |
| 50 ml SuperBlock (37515; Pierce) |
| 450 ml H$_2$O |
| 0.05% Tween |
| Test medium: |
| DMEM |
| no FCS |
| 100 IU/ml penicillin |
| 0.1 mg/ml streptomycin |
| Milk solution: |
| wash buffer |
| 5% milk powder |
| Substrate solution: |
| 1 ImmunoPure ® OPD tablet (34006; Pierce) |
| 9 ml H$_2$O |
| 1 ml stable peroxide substr. buffer, 10x (34062; Pierce) |

1st AB (P3H9-2; Santa Cruz Biotechnology, Inc.) is diluted 1/60,000 and 2nd AB (31430; Socochim S.A.) is diluted 1/500 with AB dil. soln.

Method:

The keratinocytes are sown out into 96-well plates with a density of approx. 5,000 cells/well and incubated in the culture medium for 3 days up to confluence (37° C./10% CO$_2$). The medium is exchanged for test medium with three different concentrations in triplicate of test substance. The following controls are also tested on each plate:

| Negative controls: | Positive controls: |
|---|---|
| A) with cells without 1st AB; with 2nd AB | A) with cells with 1st and 2nd AB |
| B) without cells with 1st and 2nd AB | B) with cells with 1st and 2nd AB with 10 ng/ml TGF-β2 |
| C) One well without cells is tested for each peptide in order to rule out non-specific binding of the two AB. | |

The plates are incubated for a further 72 hours. After conclusion of this incubation time, the laminin V deposited is detected and quantified in accordance with the following protocol:

Discard medium and wash with 200 µl/well of PBS fix with 100 µl/well of methanol→15 min/RT/shaker 600 rpm discard methanol and block with 200 µl/well of milk solution→30 min/RT/shaker 600 rpm discard milk solution and incubate with 100 µl/well of 1st AB dil.→2 h/RT/shaker 600 rpm discard 1st AB dil. and wash 3× with 200 µl/well of wash buffer incubate with 100 µl/well of 2nd AB dil.→3 h/RT/shaker 600 rpm discard 2nd AB dil.; wash 3× with 200 µl/well of wash buffer and 1× 100 µl/well of PBS add 100 µl/well of substrate solution→15 min/RT/shaker 600 rpm stop reaction with 50 µl/well of $H_2SO_4$ (2 M) and measure at 492 nm.

The dye solution is discarded, the plate is washed with bidist. $H_2O$ and frozen at −80° C. for approx. 16 hours.

The plate is thawed and the cell count is measured by means of the CyQUANT assay in accordance with the manufacturer's instructions.

The laminin V production per cell is calculated in accordance with the following formula: $(OD_{laminin\ V}\text{ value}/RFU_{cell\ count}\text{ value}) \times 100$ The values calculated are arbitrary units.

TABLE 2

Stimulation of laminin V in the ELISA

| No. | Substance | Conc. [µmol/l] | Stimulation in relation to control |
|---|---|---|---|
| | TGF-β (positive control) | 10 ng/ml | 40-90 |
| 1.3 | Palm-Lys-Val-Dab-OH | 25 | 34-71 |
| | | 50 | 48-75 |
| | | 100 | 64-83 |
| 1.10 | Palm-Lys-Val-Dab-NH-octyl | 2.5 | 40-45 |
| | | 5.0 | 154-200 |
| | | 10.0 | 772-940 |
| 1.11 | Palm-Lys-Val-Dab-N (octyl)$_2$ | 0.25 | 15-31 |
| | | 0.5 | 28-31 |
| | | 1.0 | 32-75 |

EXAMPLE 2

Determination of the Stimulation of Collagen IV Synthesis in Keratinocyte Cell Cultures of the Cell Line HaCaT by Treatment with the Peptide Derivatives According to the Invention The collagen IV production per cell of HaCaT keratinocytes cultured in vitro was detected by means of an ELISA (enzyme-linked immunosorbent assay). The increase in collagen IV production by the cells in the presence of the peptidic active compounds was quantified by this method. The human HaCaT keratinocytes were donated by Prof. Fusenig of the Deutsche Krebsforschungszentrum in Heidelberg and were-cultured in culture medium by standard cell culture methods. After an incubation time of 72 hours with the corresponding peptides (active compounds), the quantitative determination is carried out with an antibody specific for collagen IV. After determination of the collagen IV content, the cell count is determined by means of the CyQUANT® from Molecular Probes. The collagen IV content per cell is calculated as units from the individual values.

Material:

| Culture medium: |
|---|
| DMEM |
| 10% FCS |
| 100 IU/ml penicillin |
| 0.1 mg/ml streptomycin |
| Wash buffer: |
| 0.05 M Tris, pH 8.5 |
| 0.15 M NaCl |
| 0.1% BSA |
| 0.1% Tween 20 |
| AB dilution solution: |
| 50 ml SuperBlock (37515; Pierce) |
| 450 ml $H_2O$ |
| 0.05% Tween |
| Test medium: |
| DMEM |
| no FCS |
| 100 IU/ml penicillin |
| 0.1 mg/ml streptomycin |
| Milk solution: |
| wash buffer |
| 5% milk powder |
| Substrate solution: |
| 1 ImmunoPure ® OPD tablet (34006; Pierce) |
| 9 ml $H_2O$ |
| 1 ml stable peroxide substr. buffer, 10× (34062; Pierce) |

1st AB (H-234; Santa Cruz Biotechnology, Inc.) is diluted 1/200 and 2nd AB (31460; Socochim S.A.) is diluted 1/500 with AB dil. soln.

Method:

The keratinocytes are sown out into 96-well plates with a density of approx. 5,000 cells/well and incubated in the culture medium for 3 days up to confluence (37° C./10% $CO_2$). The medium is exchanged for test medium with three different concentrations in triplicate of test substance. The following controls are also tested on each plate:

| Negative controls: | Positive controls: |
| --- | --- |
| A) with cells without 1st AB; with 2nd AB | A) with cells with 1st and 2nd AB |
| B) without cells with 1st and 2nd AB | B) with cells with 1st and 2nd AB with 10 ng/ml TGF-β2 |
| C) One well without cells is tested for each peptide in order to rule out non-specific binding of the two AB. | |

The plates are incubated for a further 72 hours. After conclusion of this incubation time, the collagen IV deposited is detected and quantified in accordance with the following protocol:
Discard medium and wash with 200 μl/well of PBS
fix with 100 μl/well of methanol→15 min/RT/shaker 600 rpm
discard methanol and block with 200 μl/well of milk solution→30 min/RT/shaker 600 rpm
discard milk solution and incubate with 100 μl/well of 1st AB dil.→2 h/RT/shaker 600 rpm
discard 1st AB dil. and wash 3× with 200 μl/well of wash buffer
incubate with 100 μl/well of 2nd AB dil.→3 h/RT/shaker 600 rpm
discard 2nd AB dil.; wash 3× with 200 μl/well of wash buffer and 1× 100 μl/well of PBS
add 100 μl/well of substrate solution→15 min/RT/shaker 600 rpm
stop reaction with 50 μl/well of $H_2SO_4$ (2 M) and measure at 492 nm.
The dye solution is discarded, the plate is washed with bidist. $H_2O$ and frozen at −80° C. for approx. 16 hours.
The plate is thawed and the cell count is measured by means of the CyQUANT assay in accordance with the manufacturer's instructions.
The collagen IV production per cell is calculated in accordance with the following formula:

$$(OD_{collagen\ IV}\text{value}/RFU_{cell\ count}\text{value}) \times 100$$

The values calculated are arbitrary units. Compounds 1.1, 1.10, 1.11 and 2.5-2.7 from Table 1 show a good to very good stimulating action here.

EXAMPLE 3

Determination of the Stimulation of Collagen VII Synthesis in Keratinocyte Cell Cultures of the Cell Line HaCaT by Treatment with the Peptide Derivatives According to the Invention The collagen VII production per cell of HaCaT keratinocytes cultured in vitro was detected by means of an ELISA (enzyme-linked immunosorbent assay). The increase in collagen VII production by the cells in the presence of the peptidic active compounds was quantified by this method. The human HaCaT keratinocytes were donated by Prof. Fusenig of the Deutsche Krebsforschungszentrum in Heidelberg and were cultured in culture medium by standard cell culture methods. After an incubation time of 72 hours with the corresponding peptides (active compounds), the quantitative determination is carried out with an antibody specific for collagen VII. After determination of the collagen VII content, the cell count is determined by means of the CyQUANT® from Molecular Probes. The collagen VII content per cell is calculated as units from the individual values.
Material:

| Culture medium: |
| --- |
| DMEM |
| 10% FCS |
| 100 IU/ml penicillin |
| 0.1 mg/ml streptomycin |
| Wash buffer: |
| 0.05 M Tris, pH 8.5 |
| 0.15 M NaCl |
| 0.1% BSA |
| 0.1% Tween 20 |
| AB dilution solution: |
| 50 ml SuperBlock (37515; Pierce) |
| 450 ml $H_2O$ |
| 0.05% Tween |
| Test medium: |
| DMEM |
| no FCS |
| 100 IU/ml penicillin |
| 0.1 mg/ml streptomycin |
| Milk solution: |
| wash buffer |
| 5% milk powder |
| Substrate solution: |
| 1 ImmunoPure ® OPD tablet (34006; Pierce) |
| 9 ml $H_2O$ |
| 1 ml stable peroxide substr. buffer, 10× (34062; Pierce) |

1st AB (C-16; Santa Cruz Biotechnology, Inc.) is diluted 1/200 and 2nd AB (31402; Socochim S.A.) is diluted 1/500 with AB dil. soln.
Method:
The keratinocytes are sown out into 96-well plates with a density of approx. 5,000 cells/well and incubated in the culture medium for 3 days up to confluence (37° C./10% $CO_2$.). The medium is exchanged for test medium with three different concentrations in triplicate of test substance. The following controls are also tested on each plate:

| Negative controls: | Positive controls: |
| --- | --- |
| A) with cells without 1st AB; with 2nd AB | A) with cells with 1st and 2nd AB |
| B) without cells with 1st and 2nd AB | B) with cells with 1st and 2nd AB with 10 ng/ml TGF-β2 |
| C) One well without cells is tested for each peptide in order to rule out non-specific binding of the two AB. | |

The plates are incubated for a further 72 hours. After conclusion of this incubation time, the collagen VII deposited is detected and quantified in accordance with the following protocol:
Discard medium and wash with 200 μl/well of PBS
fix with 100 μl/well of methanol→15 min/RT/shaker 600 rpm discard methanol and block with 200 µl/well of milk solution→30 min/RT/shaker 600 rpm discard milk solution and incubate with 100 µl/well of 1st AB dil.→2 h/RT/shaker 600 rpm discard 1st AB dil. and wash 3× with 200 µl/well of wash buffer incubate with 100 µl/well of 2nd AB dil.→3 h/RT/shaker 600 rpm discard 2nd AB dil.; wash 3× with 200 µl/well of wash buffer and 1×100 µl/well of PBS add 100 µl/well of substrate solution→15 min/RT/shaker 600 rpm stop reaction with 50 µl/well of $H_2SO_4$ (2 M) and measure at 492 nm.

The dye solution is discarded, the plate is washed with bidist. $H_2O$ and frozen at −80° C. for approx. 16 hours.

The plate is thawed and the cell count is measured by means of the CyQUANT assay in accordance with the manufacturer's instructions.

The collagen VII production per cell is calculated in accordance with the following formula:

($OD_{collagen\ VII}$ value/$RFU_{cell\ count}$ value)×100

The values calculated are arbitrary units.

Compounds 1.10 and 2.5-2.7 from Table 1 show a good to very good stimulating action here.

EXAMPLE 4

Determination of the Stimulation of Integrin beta4 Synthesis in Keratinocyte Cell Cultures of the Cell Line HaCaT by Treatment with the Peptide Derivatives According to the Invention The integrin beta4 production per cell of HaCaT keratinocytes cultured in vitro was detected by means of an ELISA (enzyme-linked immunosorbent assay). The increase in integrin beta4 production by the cells in the presence of the peptidic active compounds was quantified by this method. The human HaCaT keratinocytes were donated by Prof. Fusenig of the Deutsche Krebsforschungszentrum in Heidelberg and were cultured in culture medium by standard cell culture methods. After an incubation time of 72 hours with the corresponding peptides (active compound), the quantitative determination is carried out with an antibody specific for integrin beta4. After determination of the integrin beta4 content, the cell count is determined by means of the CyQUANT® from Molecular Probes. The integrin beta4 content per cell is calculated as units from the individual values.

Material:

| Culture medium: |
| --- |
| DMEM |
| 10% FCS |
| 100 IU/ml penicillin |
| 0.1 mg/ml streptomycin |
| Wash buffer: |
| 0.05 M Tris, pH 8.5 |
| 0.15 M NaCl |
| 0.1% BSA |
| 0.1% Tween 20 |
| AB dilution solution: |
| 50 ml SuperBlock (37515; Pierce) |
| 450 ml $H_2O$ |
| 0.05% Tween |
| Test medium: |
| DMEM |
| no FCS |
| 100 IU/ml penicillin |
| 0.1 mg/ml streptomycin |
| Milk solution: |
| wash buffer |
| 5% milk powder |
| Substrate solution: |
| 1 ImmunoPure ® OPD tablet (34006; Pierce) |
| 9 ml $H_2O$ |
| 1 ml stable peroxide substr. buffer, 10x(34062; Pierce) |

1st AB (C-16; Santa Cruz Biotechnology, Inc.) is diluted 1/200 and 2nd AB (31402; Socochim S.A.) is diluted 1/500 with AB dil. soln.

Method:

The keratinocytes are sown out into 96-well plates with a density of approx. 5,000 cells/well and incubated in the culture medium for 3 days up to confluence (37° C./10% $CO_2$). The medium is exchanged for test medium with three different concentrations in triplicate of test substance. The following controls are also tested on each plate:

| Negative controls: | Positive controls: |
| --- | --- |
| A) with cells without 1st AB; with 2nd AB | A) with cells with 1st and 2nd AB |
| B) without cells with 1st and 2nd AB | B) with cells with 1st and 2nd AB with 10 ng/ml TGF-β2 |
| C) One well without cells is tested for each peptide in order to rule out non-specific binding of the two AB. | |

The plates are incubated for a further 72 hours. After conclusion of this incubation time, the integrin β4 deposited is detected and quantified in accordance with the following protocol:

Discard medium and wash with 200 µl/well of PBS fix with 100 µl/well of methanol→15 min/RT/shaker 600 rpm discard methanol and block with 200 µl/well of milk solution→30 min/RT/shaker 600 rpm discard milk solution and incubate with 100 µl/well of 1st AB dil.→2 h/RT/shaker 600 rpm a discard 1st AB dil. and wash 3× with 200 µl/well of wash buffer incubate with 100 µl/well of 2nd AB dil.→3 h/RT/shaker 600 rpm discard 2nd AB dil.; wash 3× with 200 µl/well of wash buffer and 1×100 µl/well of PBS add 100 µl/well of substrate solution→15 min/RT/shaker 600 rpm stop reaction with 50 µl/well of $H_2SO_4$ (2 M) and measure at 492 nm.

The dye solution is discarded, the plate is washed with bidist. $H_2O$ and frozen at −80° C. for approx. 16 hours.

The plate is thawed and the cell count is measured by means of the CyQUANT assay in accordance with the manufacturer's instructions.

The integrin β4 production per cell is calculated in accordance with the following formula:

$$(OD_{integrin\ \beta 4}\ value/RFU_{cell\ count}\ value) \times 100$$

The values calculated are arbitrary units.

Compounds 1.1 and 2.5-2.7 from Table 1 show a good to very good stimulating action here.

EXAMPLE 5

Determination of the Stimulation of Collagen XVII Synthesis in Keratinocyte Cell Cultures of the Cell Line HaCaT by Treatment with the Peptide Derivatives According to the Invention The collagen XVII production per cell of HaCaT keratinocytes cultured in vitro was detected by means of an ELISA (enzyme-linked immunosorbent assay). The increase in collagen XVII production by the cells in the presence of the peptidic active compounds was quantified by this method. The human HaCaT keratinocytes were donated by Prof. Fusenig of the Deutsche Krebsforschungszentrum in Heidelberg and were cultured in culture medium by standard cell culture methods. After an incubation time of 72 hours with the corresponding peptides (active compounds), the quantitative determination is carried out with an antibody specific for collagen XVII. After determination of the collagen XVII content, the cell count is determined by means of the CyQUANT® from Molecular Probes. The collagen XVII content per cell is calculated as units from the individual values.

Material:

---
Culture medium:

DMEM
10% FCS
100 IU/ml penicillin
0.1 mg/ml streptomycin

Wash buffer:

0.05 M Tris, pH 8.5
0.15 M NaCl
0.1% BSA
0.1% Tween 20

AB dilution solution:

50 ml SuperBlock (37515; Pierce)
450 ml $H_2O$
0.05% Tween

Test medium:

DMEM
no FCS
100 IU/ml penicillin
0.1 mg/ml streptomycin

Milk solution:

wash buffer
5% milk powder

Substrate solution:

1 ImmunoPure ® OPD tablet (34006; Pierce)
9 ml $H_2O$
1 ml stable peroxide substr. buffer, 10x(34062; Pierce)
---

1st AB (STO-115; Davids Biotechnology) is diluted 1/200 and 2nd AB (31430; Socochim S.A.) is diluted 1/500 with AB dil. soln.

Method:

The keratinocytes are sown out into 96-well plates with a density of approx. 5,000 cells/well and incubated in the culture medium for 3 days up to confluence (37° C./10% $CO_2$). The medium is exchanged for test medium with three different concentrations in triplicate of test substance. The following controls are also tested on each plate:

| Negative controls: | Positive controls: |
|---|---|
| A) with cells without 1st AB; with 2nd AB | A) with cells with 1st and 2nd AB |
| B) without cells with 1st and 2nd AB | B) with cells with 1st and 2nd AB with 10 ng/ml TGF-β2 |
| C) One well without cells is tested for each peptide in order to rule out non-specific binding of the two AB. | |

The plates are incubated for a further 72 hours. After conclusion of this incubation time, the collagen XVII deposited is detected and quantified in accordance with the following protocol:

Discard medium and wash with 200 μl/well of PBS fix with 100 μl/well of methanol→15 min/RT/shaker 600 rpm discard methanol and block with 200 μl/well of milk solution→30 min/RT/shaker 600 rpm discard milk solution and incubate with 100 μl/well of 1st AB dil.→2 h/RT/shaker 600 rpm discard 1st AB dil. and wash 3× with 200 μl/well of wash buffer incubate with 100 μl/well of 2nd AB dil.→3 h/RT/shaker 600 rpm discard 2nd AB dil.; wash 3× with 200 μl/well of wash buffer and 1×100 μl/well of PBS add 100 μl/well of substrate solution→15 min/RT shaker 600 rpm stop reaction with 50 μl/well of $H_2SO_4$ (2 M) and measure at 492 nm.

The dye solution is discarded, the plate is washed with bidist. $H_2O$ and frozen at −80° C. for approx. 16 hours.

The plate is thawed and the cell count is measured by means of the CyQUANT assay in accordance with the manufacturer's instructions.

The collagen XVII production per cell is calculated in accordance with the following formula:

$$(OD_{collagen\ XVII}\ value/RFU_{cell\ count}\ value) \times 100$$

The values calculated are arbitrary units.

Compounds 1.1, 1.10, 1.11 and 2.5-2.7 show a good to very good stimulating action here.

EXAMPLE 6

Formulation of an Ointment

Procedure: Constituents 1-5 (A) are heated to 70° C. Constituents 6-7 (B) are heated to 75° C. B is added to A, with stirring, and the mixture is cooled to 50° C., homogenized and cooled to 30° C. Constituents 8 and 9 (C) and constituents and 11 (D) are then added in succession and the mixture is stirred cold.

| Number | Constituent | % w/w |
|---|---|---|
| 1 | (A) Tego Care 450 | 3.00 |
| 2 | Cetearyl alcohol | 2.25 |
| 3 | Glyceryl stearate | 2.25 |
| 4 | Cetiol 868 | 10.00 |
| 5 | Squalane | 5.00 |
| 6 | (B) Deionized water | 66.995 |
| 7 | Sodium hyaluronate | 5.00 |
| 8 | (C) Glycerol | 5.00 |
| 9 | Phenonip | 0.5 |
| 10 | (D) Palm-Lys-Val-Dab-OH (1.3) | 0.0025 |
| 11 | Palm-Lys-Val-Dab-Thr-OH (2.7) | 0.0025 |

EXAMPLE 7

Formulation of a Gel

Procedure: Constituents 2-6 (A) are dissolved in succession in deionized water. The solution is adjusted to pH 6.0 with constituent 7 (B). Constituents 8 and 9 (C) are then added.

| Number | Constituent | % w/w |
|---|---|---|
| 1 | (A) Deionized water | 92.095 |
| 2 | 1,3-Butanediol | 5.00 |
| 3 | Phenonip | 0.50 |
| 4 | Abil B 8843 | 1.50 |
| 5 | Carboxymethylcellulose | 0.15 |
| 6 | Carbopol Ultrez 10 | 0.75 |
| 7 | (B) NaOH | |
| 8 | (C) Palm-Lys-Val-Dab-OH (1.3) | 0.0025 |
| 9 | Palm-Lys-Val-Dab-Thr-OH (2.7) | 0.0025 |

EXAMPLE 8

Preparation of Compounds According to the Invention of the Formula (I) Wherein X Denotes —NR$^2$— and Both R$^1$ and R$^2$ are Other than H, and of Compounds According to the Invention Corresponding to the Formula (I), but Wherein XR$^1$ with X in the Possible Meaning —NH— Denotes the Radical of an Alpha-Amino Acid, and of Salts of Such Compounds The analysis of the eluates and products obtained according to this example was performed with proton NMR, HPLC-electrospray MS or elemental analysis. The compounds can be prepared by the processes known per se described in the following (general instructions of M. Bodanszky "The Practice of Peptide Synthesis" Springer Verlag, 2nd edition 1994). The amino acid, for example lysine, is accordingly linked to a resin in a solid phase synthesis on the carboxy-terminal end, the amino group thereof being protected by a protective group, e.g. by the Fmoc protective group. The side chain is protected e.g. with Boc or t-butyl. The protective groups are split off selectively as required, in order to link the further amino acid derivatives with the conventional reagents in peptide synthesis until the desired sequence is built up completely. The peptide is then split off from the resin on the carboxy-terminal end and the crude peptide is precipitated by dropwise addition into a suitable solvent mixture. The mixture is purified via HPLC, optionally exchanged into the counter-ions and the substance is lyophilized

EXAMPLE 8.1

Preparation of Palm-Lys(Boc)-Val-Dab(Boc)-Thr (tBu)-CTR on a Solid Phase

The protected amino acids Fmoc-Thr(tBu)-OH, Fmoc-Dab(Boc)-OH, Fmoc-Val-OH, Fmoc-Lys(Boc)-OH and palmitic acid are linked to 1.75 g (loading: 0.8 mmol/g) of 2-chlorotrityl chloride resin by successive peptide linkings and the protected peptide is built up in this way.

EXAMPLE 8.2

Preparation of Palm-Lys-Val-Dab-Thr-OH.2TFA on a Solid Phase

The peptide is split off from the resin by means of treatment with 10 ml of 95% TFA for 30 minutes. The resin is filtered off and the solution is added dropwise into 100 ml of Et$_2$O. The precipitate formed is filtered off with suction, washed and, after drying, purified with the aid of preparative HPLC and then lyophilized. 391 mg (34%) of a colourless powder are obtained. The theoretical mass of 686 was confirmed with a finding of 687.

EXAMPLE 8.3

Preparation of Compounds According to the Invention of the Formula (I) Wherein X Denotes —NR$^2$— and Both R$^1$ and R$^2$ are Other than H Such compounds can be prepared analogously to the process described in Example 7 of WO 2004/099237 A1.

The invention claimed is:
1. A method of stimulating the synthesis of molecules of the basement membrane, which method comprises administering to a person in need of such stimulation a composition containing an effective amount of at least one compound of the following formula (I) together with at least one compound corresponding to the following formula (I), but wherein XR$^1$ with X in the possible meaning —NH— denotes the radical of an alpha-amino acid, and wherein the composition can be applied topically;

formula (I):

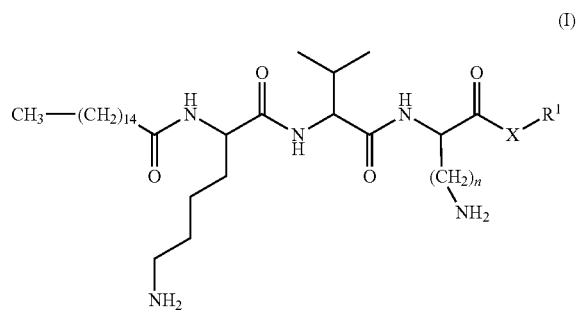

wherein
R$^1$ denotes H, C$_1$-C$_{20}$-alkyl;
n denotes 2;
X denotes —O—, —NH— or —NR$^2$—; and
R$^2$ denotes H or C$_1$-C$_{20}$-alkyl.

2. The method according to claim 1 for stimulating the synthesis of molecules of the basement membrane, wherein said molecules are proteins of the basement membrane.

3. The method according to claim 1, wherein said method stimulates the synthesis of laminin V, the synthesis of collagen IV, the synthesis of collagen VII, the synthesis of collagen XVII and the synthesis of integrin β4 of the basement membrane.

4. The method according to claim 2, wherein said method improves flabby, rough and wrinkled skin caused by endogenous or exogenous degeneration of the basement membrane.

5. The method according to claim 2, wherein said method slows down the formation of flabby, rough and wrinkled skin.

6. The method according to claim 2, wherein said method further comprises administering the composition to said person in combination with at least one additional skin care active compound.

7. The method of claim 1 wherein said alpha-amino acid is selected from the group consisting of Glu, Asp and Thr.

8. The method according to claim 7 for stimulating the synthesis of molecules of the basement membrane, wherein said molecules are proteins of the basement membrane.

9. The method according to claim 7, wherein said method stimulates the synthesis of laminin V, the synthesis of collagen IV, the synthesis of collagen VII, the synthesis of collagen XVII and the synthesis of integrin β4 of the basement membrane.

10. The method according to claim 8, wherein said method improves flabby, rough and wrinkled skin caused by endogenous or exogenous degeneration of the basement membrane.

11. The method according to claim 8, wherein said method slows down the formation of flabby, rough and wrinkled skin.

12. The method according to claim 8, wherein said method further comprises administering the composition to said person in combination with at least one additional skin care active compound.

* * * * *